United States Patent
Rassman et al.

(10) Patent No.: US 7,518,724 B2
(45) Date of Patent: *Apr. 14, 2009

(54) IMAGE ACQUISITION, PROCESSING, AND DISPLAY

(75) Inventors: William R. Rassman, Los Angeles, CA (US); David Ralin, South Pasadena, CA (US); Jason D. Berger, Los Angeles, CA (US); Robert A. Lieberman, Torrance, CA (US); Lothar U. Kempen, Redondo Beach, CA (US)

(73) Assignee: Maven Technologies, Los Angeles, CA (US)

( * ) Notice: Subject to any disclaimer, the term of this patent is extended or adjusted under 35 U.S.C. 154(b) by 271 days.

This patent is subject to a terminal disclaimer.

(21) Appl. No.: 11/321,168

(22) Filed: Dec. 29, 2005

(65) Prior Publication Data

US 2007/0058166 A1 Mar. 15, 2007

Related U.S. Application Data

(63) Continuation-in-part of application No. 09/838,700, filed on Apr. 19, 2001, now Pat. No. 7,023,547, which is a continuation-in-part of application No. 09/614,503, filed on Jul. 11, 2000, now Pat. No. 6,594,011.

(51) Int. Cl.
*G01J 4/00* (2006.01)
*G01B 11/30* (2006.01)
(52) U.S. Cl. .................. 356/369; 356/612; 356/390
(58) Field of Classification Search ............ None
See application file for complete search history.

(56) References Cited

U.S. PATENT DOCUMENTS

| 1,637,141 A | 7/1927 | Cooper |
| 3,415,825 A | 12/1968 | Yoshikazu |
| 3,858,616 A | 1/1975 | Thiery et al. |
| 4,238,565 A | 12/1980 | Hornby et al. |

(Continued)

FOREIGN PATENT DOCUMENTS

AU 742417 2/2000

(Continued)

OTHER PUBLICATIONS

Tadashi Saitoh, et al. "Optical Characterization of Very Thin Hydrogenated Amorphous Silicon Films Using Spectroscopic Ellipsometry"; Japanese Journal of Applied Physics; vol. 30, No. 11B, Nov. 1991, pp. L1914-L1916.

(Continued)

*Primary Examiner*—L. G Lauchman
*Assistant Examiner*—Rebecca C Slomski
(74) *Attorney, Agent, or Firm*—Haynes and Boone, LLP.

(57) ABSTRACT

Image data is acquired, processed, and/or displayed in accordance with an embodiment of the present disclosure to display, monitor, and/or demonstrate the progress of an experiment substantially in real-time and with high sensitivity. In one embodiment, at least one time-resolved value of spatially distributed polarization change data is provided and displayed. Advantageously, real-time processing and display of data is provided such that discussion and collaboration about the experiment may occur, time-resolved data is not lost, and resources are not wasted.

15 Claims, 14 Drawing Sheets

U.S. PATENT DOCUMENTS

| | | | |
|---|---|---|---|
| 4,256,834 A | 3/1981 | Zuk et al. | |
| 4,508,832 A | 4/1985 | Carter et al. | |
| 5,164,589 A | 11/1992 | Sjoedin | |
| 5,229,833 A | 7/1993 | Stewart | |
| 5,234,769 A | 8/1993 | Shevlin | |
| 5,255,075 A | 10/1993 | Cush | |
| 5,313,264 A | 5/1994 | Ivarsson et al. | |
| 5,341,215 A * | 8/1994 | Seher | 356/445 |
| 5,437,840 A | 8/1995 | King et al. | |
| 5,446,534 A * | 8/1995 | Goldman | 356/128 |
| 5,483,346 A | 1/1996 | Butzer | |
| 5,485,277 A * | 1/1996 | Foster | 356/445 |
| 5,491,097 A | 2/1996 | Ribi et al. | |
| 5,491,556 A | 2/1996 | Stewart et al. | |
| 5,573,956 A | 11/1996 | Hanning | |
| 5,593,130 A | 1/1997 | Hansson et al. | |
| 5,633,724 A | 5/1997 | King et al. | |
| 5,641,640 A | 6/1997 | Hanning | |
| RE35,715 E | 1/1998 | Stapleton et al. | |
| 5,753,518 A | 5/1998 | Karlsson | |
| 5,796,858 A | 8/1998 | Zhou et al. | |
| 5,813,439 A | 9/1998 | Herrero et al. | |
| 5,856,873 A | 1/1999 | Naya et al. | |
| 5,922,594 A | 7/1999 | Loefas | |
| 5,922,604 A | 7/1999 | Stapleton et al. | |
| 5,955,729 A | 9/1999 | Nelson et al. | |
| 5,965,456 A | 10/1999 | Malmqvist et al. | |
| 5,972,612 A | 10/1999 | Malmqvist et al. | |
| 6,008,010 A | 12/1999 | Greenberger et al. | |
| 6,008,893 A | 12/1999 | Roos et al. | |
| 6,026,053 A | 2/2000 | Satorius | |
| 6,045,996 A | 4/2000 | Cronin et al. | |
| 6,065,501 A | 5/2000 | Feret et al. | |
| 6,127,183 A | 10/2000 | Ivarsson et al. | |
| 6,140,044 A | 10/2000 | Besemer et al. | |
| 6,143,513 A | 11/2000 | Loefas | |
| 6,143,574 A | 11/2000 | Karlsson et al. | |
| 6,197,595 B1 | 3/2001 | Anderson et al. | |
| 6,200,814 B1 | 3/2001 | Malmqvist et al. | |
| 6,207,381 B1 | 3/2001 | Larsson et al. | |
| 6,253,793 B1 | 7/2001 | Dupoiron et al. | |
| 6,277,330 B1 | 8/2001 | Liu et al. | |
| 6,289,286 B1 | 9/2001 | Andersson et al. | |
| 6,354,333 B1 | 3/2002 | Dupoiron et al. | |
| 6,355,429 B1 | 3/2002 | Nygren et al. | |
| 6,475,809 B1 | 11/2002 | Wagner et al. | |
| 6,493,097 B1 | 12/2002 | Ivarsson | |
| 6,503,760 B2 | 1/2003 | Malmqvist et al. | |
| D472,644 S | 4/2003 | Dawson et al. | |
| 6,549,011 B2 | 4/2003 | Flatt | |
| 6,589,798 B1 | 7/2003 | Loefas | |
| 6,594,011 B1 | 7/2003 | Kempen | |
| D480,149 S | 9/2003 | Dawson et al. | |
| 6,698,454 B2 | 3/2004 | Sjoelander et al. | |
| 6,710,870 B1 | 3/2004 | Marowsky et al. | |
| 6,806,051 B2 | 10/2004 | Ellson | |
| 6,810,286 B2 | 10/2004 | Donovan et al. | |
| 6,833,920 B2 | 12/2004 | Rassman et al. | |
| 6,859,280 B2 | 2/2005 | Kempen | |
| 6,882,420 B2 | 4/2005 | Rassman et al. | |
| 6,981,526 B2 | 1/2006 | Glejbol et al. | |
| 7,045,287 B2 | 5/2006 | Smith et al. | |
| 7,193,711 B2 | 3/2007 | Rassman et al. | |
| 2002/0019019 A1 | 2/2002 | Hamalainen et al. | |
| 2002/0154311 A1 | 10/2002 | Ivarsson | |
| 2002/0182717 A1 | 12/2002 | Karlsson | |
| 2003/0022388 A1 | 1/2003 | Roos et al. | |
| 2003/0067612 A1 | 4/2003 | Ivarsson | |
| 2003/0112432 A1 | 6/2003 | Yguerabide et al. | |
| 2003/0205681 A1 | 11/2003 | Modlin | |
| 2004/0002167 A1 | 1/2004 | Andersson et al. | |
| 2004/0012676 A1 | 1/2004 | Weiner et al. | |
| 2004/0023247 A1 | 2/2004 | Xu et al. | |
| 2004/0030504 A1 | 2/2004 | Helt et al. | |
| 2004/0038268 A1 | 2/2004 | Pirrung et al. | |
| 2005/0148063 A1 | 7/2005 | Cracauer et al. | |

FOREIGN PATENT DOCUMENTS

| | | |
|---|---|---|
| WO | WO 89/11057 | 11/1989 |
| WO | WO 91/00467 | 1/1991 |
| WO | WO 96/08720 | 3/1996 |
| WO | WO 96/38729 | 12/1996 |
| WO | WO 97/19375 | 5/1997 |
| WO | WO 98/32002 | 7/1998 |
| WO | WO 03/056337 A1 | 7/2003 |
| WO | WO 03/102580 A1 | 12/2003 |

OTHER PUBLICATIONS

"Handbook of Optics", Michael Bass Editor in Chief, by The Optical Society of America; vol. 1; pp. 4.23, 4.24; 1995 McGraw-Hill, Inc.

Bass, et al. "Handbook of Optics", by The Optical Society of America; vol. 1; Section 41.10; 1995 McGraw-Hill, Inc.

Gang Jin et al. "Imaging Ellipsometry Revisited: Developments for Visualization of Thin Transparent Layers on Silicon Substrates", American Institute of Physics, Rev. Sci. Instrum., pp. 2930-2936, Aug. 1996.

Max Born et al. "Principles of Optics—Electromagnetic Theory of Propagation, Interference and Diffraction of Light", Sixth Edition, pp. 47-51 Pergamon Press No Date.

Eggins, "Biosensors: An Introduction", pp. 112-113, 1987 John Wiley & Sons No Date.

Danny Van Noort et al. "Monitoring Specific Interaction of Low Molecular Weight Biomolecules on Oxidized Porous Slicon Ellipsometry", Biosensors & Bioelectronics vol. 13, No. 3-4 pp. 439-449, 1998 Elsevier Science, S.A. Great Britain.

Gang Jin et al. "Imaging Ellipsometry for Biosensor Applications" Transducers '95, Eurosensors IX, Digest of Technical Papers vol. 2, Sessions A7-D13, Papers No. 232-496 pp. 509-512, Stockholm, Sweden, Jun. 1995.

Jinyu Wang "Waveguide Ellipsometry Biosensors: Concept and Preliminary Analysis", SPIE vol. 1648, Fiber Optical Medical and Fluorescent Sensors and Applications pp. 44-50, 1992.

Ulf Jonsson et al. "Flow-Injection Ellipsometry—An in Situ Method for the Study of Biomolecular Adsorption and Interaction at Solid Surfaces," Colloids and Surfaces, 13 (1985) pp. 333-339, 1985 Elsevier Science Publishers BV, Amsterdam, The Netherlands.

Jonsson, Ulf et al. "Biosensors Based on Surface Concentration Measuring Devices-The Concept of Surface Concentration" Progress in Colloid and Polymer Sci. vol. 70, pp. 96-100, 1985.

Schena, Mark "DNA Microarrays: A Practical Approach" Edited by Mark Schena, Department of Biochemistry, Beckman Center, Stanford University Medical Center, Stanford, USA, Oxford University Press, 1999.

Schema, PhD. Mark, "Microarray Biochip Technology" TeleChem International, Inc., Sunnyvale, California, USA, A BioTechniques Books Publication, Eaton Publishing, pp. 10-11, 2000.

Harland G. Tompkins, et al. "Spectroscopic Ellipsometry and Reflectometry A User's Guide" A Wiley-Interscience Publication, John Wiley & Sons, Inc., 1999.

Ulf Jonsson et al. "Surface Immobilization Techniques in Combination with Ellipsometry" Methods in Enzymology vol. 137, Immobilized Enzymes and Cells Part D pp. 381-1351, 1988 Academic Press, Inc. Harcourt Brace Jovanovich, Publishers.

CH Striebel et al. "Characterization of Biomembranes by Spectral Ellipsometry, Surface Plasmon Resonance and Interferometry with Regard to Biosensor Application", Biosensors & Bioelectronics 9, pp. 139-146, 1994 Elsevier Science Publishers Ltd.

T.A. Ruzgas et al. "Ellipsometric Immunosensors for the Determination of γ-Interferon and Human Serum Albumin", Biosensors & Bioelectronics 7, pp. 305-308, 1992 Elsevier Science Publishers Ltd.

Haken Nygren et al. "Determination by Ellipsometry of the Affinity of Monoclonal Antibodies", Journal of Immunological Methods, 92, pp. 219-225, 1986 Elsevier Science Publishers Ltd. 1992.

John F. Place et al. "Opto-electronic Immunosensors: A Review of Optical Immunoassay At Continuous Surfaces", Biosensors 1, pp. 321-353, 1985 Elsevier Applied Science Publishers Ltd., England.

A. Brecht et al. "Biosensors: Fundamentals, Technologies and Applications" GBF Monographs, vol. 17, pp. 174-178, 1991 Germany.

Hakan Nygren et al., "Kinetics of Antibody-Binding to Surface-Immobilized Antigen: Influence of Mass Transport on the Enzyme-Linked Immunosorbent Assay (ELISA)", Journal of Colloid and Interface Science, vol. 107, No. 2 pp. 560-566, Oct. 1985 Academic Press, Inc.

Martin Malmsten et al. "Effects of Hydrophilization and Immobilization on the Interfacial Behavior of Immunoglobulins", Journal of Colloid and Interface Sicence 177, pp. 70-78, 1996 Academic Press, Inc. No Date.

Pentti Tengvall et al. "Temporal Studies on the Deposition of Complement on Human Colostrum IgA and Serum Immobilized on Methylated Silicon", Journal of Biomedical Materials Research, vol. 35, pp. 81-91, 1997 John Wiley & Sons, Inc.

Huaiyou Wang et al. "Assembly of Antibodies in Lipid Membranes for Biosensor Development", Applied Biochemistry and Biotechnology, vol. 53 pp. 163-181, 1995 Humana Press Inc.

G. Elender et al. "Wetting and Dewetting of Si/SiO2-Wafers by Free and Lipid-Monolayer Covered Aqueous Solutions Under Controlled Humidity", Journal de Physique, II France 4 pp. 455-479, Mar. 1994.

C.F. Mandenius et al. "Coupling of Biomolecules to Silicon Surfaces for use in ellipsometry and other related techniques", Methods in Enzymology, vol. 137, pp. 389-394, 1988 Academic Press, Inc.

A.W. Flounders et al. "Patterning of immobilized antibody layers via photolithography and oxygen plasma exposure", Biosensors and Bioelectronics, vol. 12, No. 6 pp. 447-456, 1997 Elsevier Science Ltd. Great Britain.

A. Ahluwalia et al. "A comparative study of protein immobilization techniques for optical immunosensors", Biosensors and Bioelectronics 7, (1991) pp. 207-214, 1992 Elsevier Science Publishers Ltd.

Dr. Rudolf Oldenbourg "Metamorph Imaging System", http://www.image1.com/products/metapolscope/ Universal Imaging Corporation Last Updated Jun. 10, 1999 pp. 1-2.

Dr. Rudolf Oldenbourg "A new view on polarization microscopy", Nature, vol. 381, pp. 811-812, Jun. 27, 1996.

Clifford C. Hoyt et al. "Structural analysis with quantitative birefringence imaging", American Laboratory, pp. 34-42, Jul. 1999.

Dirk Honig et al. "Direct visualization of monolayers at the air-water interface by Brewster angle microscopy", J. Phys. Chem., pp. 4590 & 4592, 1991 American Chemical Society.

S. Henon et al. "Microscope at the Brewster angle: direct observation of first-order phase transitions in monolayers", Rev. Sci. Instrum. 62, (4) pp. 936-939, Apr. 1991 American Institute of Physics.

Gang Jin et al. "A biosensor concept based on imaging ellipsometry for visualization of biomolecular interactions", Analytical Biochemistry 232, pp. 69-72, 1995.

Pentti Tengvall et al. "Complement activation by 3-mercapto-1,2-propanediol immobilized on gold surfaces", Biomaterials vol. 17, No. 10 pp. 1001-1007, 1995 Elseviar Science Ltd., Great Britain.

H. Arwin "Spectroscopic ellipsometry and biology: recent developments and challenges", Thin Solid Films 313-314, pp. 7640774, 1998 Elsevier Science S.A.

Christopher Palmer "Diffraction Grating Handbook", pp. 35-44, 2000 Richardson Grating Laboratory, Rochester, New York.

Erwin G. Loewen "Diffraction Gratings, Ruled and Holographic", Applied Optics and Optical Engineering, vol. IX, pp. 33-71, Bausch and Lomb, Inc., Rochester, New York 1983 Academic Press, Inc.

Willems, Goerge M., et al., Adsorption and Conversion of Prothrombin on a Rotating Disc, Blood, Jul. 15, 1993, vol. 82, No. 2, pp. 497-504.

* cited by examiner

TIFF Image t0000

TIFF Image t1440

Differential TIFF Image t1440 minus t0000

Histogram of t1440 TIFF Image

Histogram of Differential TIFF Image

IMAGE ACQUISITION, PROCESSING, AND DISPLAY

CROSS-REFERENCE TO RELATED APPLICATIONS

This application is a continuation-in-part of U.S. patent application Ser. No. 09/838,700 filed on Apr. 19, 2001 now U.S. Pat. No. 7,023,547, which is a continuation-in-part of U.S. patent application Ser. No. 09/614,503, filed on Jul. 11, 2000, now U.S. Pat. No. 6,594,011, the full disclosures of which are incorporated by reference herein for all purposes.

This application is related to U.S. patent application Ser. No. 10/847,754 filed on May 17, 2004, U.S. patent application Ser. No. 10/847,736 filed on May 17, 2004, U.S. patent application Ser. No. 10/841,988 filed on May 7, 2004, and U.S. patent application Ser. No. 10/046,620 filed on Jan. 12, 2002. The above-mentioned U.S. patent application Ser. Nos. 10/847,754, 10/847,736, 10/841,988, and 10/046,620 are incorporated by reference herein for all purposes.

BACKGROUND

1. Field of Invention

This invention relates to acquisition and processing of data and more particularly to acquisition and processing of microarray data for displaying, monitoring, and/or demonstrating the progress of an experiment substantially in real-time.

2. Discussion of the Related Art

The formation of an array of biologically or chemically active spots on the surface of a substrate for identifying constituents in test material brought into contact with the array is known, such as with a biochip (also referred to as a gene chip, protein chip, microarray, and others). Typically, such processes require spots of, for example, oligonucleotides, cloned DNA, antibodies, peptides, receptors, enzymes, and/or inhibitors, which are processed to exhibit characteristics such as fluorescence, electroluminescence, current change, and/or voltage change, for providing a detectable signature for the presence of constituents in the material being tested.

Typically, microarray experiments have been analyzed at or near the approximate endpoint of reactions, which is presumed to be equilibrium, and real-time and/or time-resolved information have not been provided. Disadvantageously, such endpoint analysis does not allow for monitoring of or collaboration about the process under investigation, thus losing kinetic data, affinity data, and other time-resolved data regarding the process. Such endpoint analysis also does not allow for modification or early termination of the experiment if an error occurs, thus wasting time and resources.

Thus, there is a need for a method and apparatus to gather, process, and display image data which is highly sensitive and substantially at real-time and/or time-resolved.

SUMMARY

Image data is acquired and processed in accordance with an embodiment of the present invention to display, monitor, and/or demonstrate the progress of an experiment substantially in real-time and with high sensitivity. Advantageously, the present invention allows for real-time processing and display of data such that discussion and collaboration about the experiment may occur, time-resolved data is not lost, and resources are not wasted.

In accordance with one embodiment of the present invention, an image processor is provided, including a data acquisition application adapted to receive spatially distributed polarization change data caused by a specimen array; and a data analyzer operably coupled to the data acquisition application, the data analyzer adapted to calculate at least one time-resolved value of the spatially distributed polarization change data.

In accordance with another embodiment of the present invention, an apparatus for imaging is provided, including a light source emitting a polarized light beam; an optical assembly including a light reflection surface, wherein the light beam from the light source is reflected by the light reflection surface to provide an evanescent field adjacent the light reflection surface, the light reflection surface being adapted to allow placing thereon a specimen array such that the specimen array in the evanescent field causes spatially distributed polarization changes in the cross-section of the light beam; and a two-dimensional array detector positioned to detect the spatially distributed polarization changes caused by the specimen array. A processor is operably coupled to the two-dimensional array detector, the processor processing data from the two-dimensional array detector to provide a two-dimensional representation of the spatially distributed polarization changes occurring in the specimen array in real-time.

In accordance with yet another embodiment of the present invention, a method of processing image data is provided, including receiving spatially distributed polarization change data caused by a specimen array; and calculating at least one time-resolved value of the spatially distributed polarization change data.

In accordance with yet another embodiment of the present invention, a method of imaging is provided, including passing a polarized light beam into an optical assembly including a control layer and a light reflection surface to provide an evanescent field with controlled height and intensity adjacent the light reflection surface, a specimen array in the evanescent field causing spatially distributed polarization changes in the cross-section of the light beam; passing the reflected light beam out of the optical structure; and detecting the spatially distributed polarization changes caused by the specimen array. The method further includes processing the detected spatially distributed polarization changes to provide a two-dimensional representation of the spatially distributed polarization changes occurring in the specimen array in real-time.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

Figure 1:
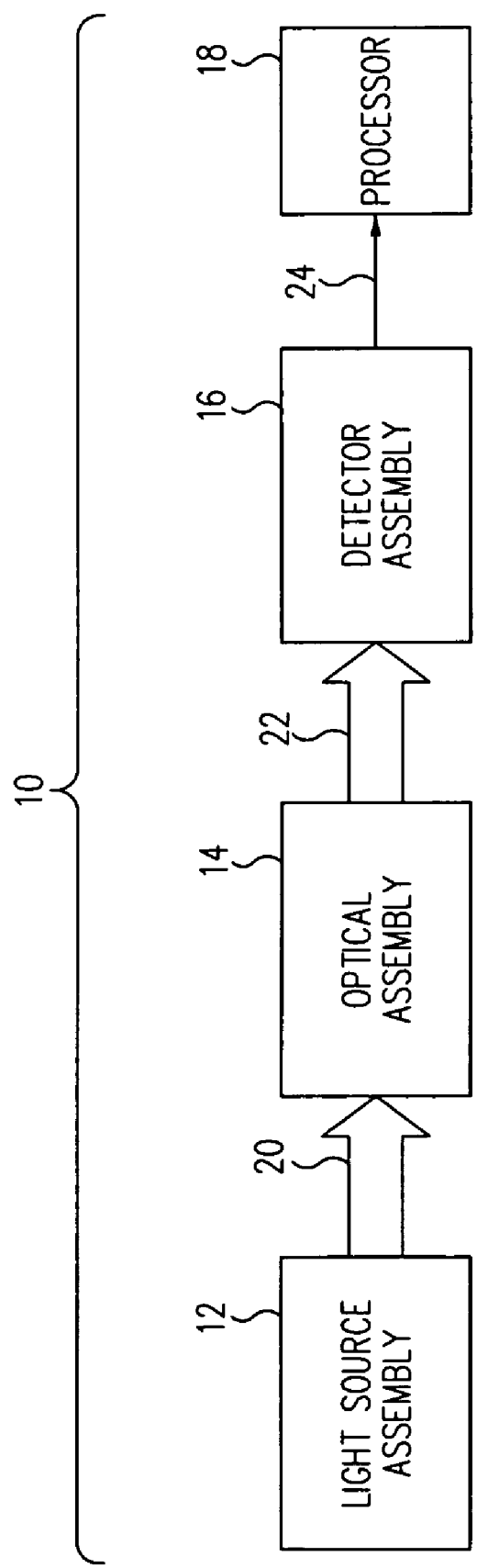
FIG. 1 is a block diagram of an illustrative system in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The invention generally comprises a method and apparatus for acquiring, processing, and displaying data, and in one embodiment relates to acquiring, processing, and display of data from a two-dimensional arrangement of chemical substances obtained by an imaging technique and apparatus, such as that disclosed in U.S. Pat. No. 6,594,011, the contents of which have been previously incorporated by reference.

In one embodiment, a polarized light source of known polarization state is directed into an optical assembly, for example a total internal reflection member (TIR member), configured for a reflection at a light reflection surface, for example a total internal reflection surface (TIR surface), and then allowed to exit the optical assembly. In the context of this document, superposition of reflections as encountered at a layered optical structure where the layer thicknesses are smaller than the coherence length of the illuminating light is referred to as a single reflection.

The chemical specimen is in place above the light reflection surface in the evanescent field of the reflected light beam. After reflection, the beam is passed to a polarization-sensitive two-dimensional detector such as a polarizer and a camera or other types of detectors. The beam's content can then be processed to determine the change in polarization state, locally in the two-dimensional cross-section of the beam. This provides a spatially distributed map of change of polarization state in the specimen. A variety of techniques are available to determine the change in polarization such as measuring the deviation from a null condition or by comparing the input polarization state to the output polarization state.

The refractive index composition of the materials within the evanescent field determines the change in the polarization state of the beam due to the reflection at the light reflection surface. A two-dimensional variation of this composition within the light reflection surface is associated with a respective variation of the polarization state spatially distributed across the cross-section of the reflected light beam.

In one application, the chemical specimen forms a two-dimensional array of molecules (referred to herein as receptors and generally referred to as capture agents or affinity agents) with specific affinities towards respective other molecules (referred to herein as ligands). In this application, the invention is utilized to indicate the presence or absence or rate of binding between ligands and receptors on the array. Such arrays commonly consist of a plurality of discrete specimen spots. The present method and apparatus images the array so as to distinguish each of the discrete specimen spots represented by the local change in polarization state in the cross-section of the reflected beam.

Measurements are designed for maximum practical sensitivity and triggered at discrete intervals appropriate for the experiment, determined by a three-component analysis based on the affinity constants, size, and concentration of the analytes. Data is culled for conservation of computing and storage resources. If, for instance, it is known that the sample system contains low-affinity components, generally longer incubation or dwell time is required. If size of the analyte is small, maximum sensitivity settings of the instrument are required which in turn generally requires longer measurements and correspondingly longer intervals. If the concentration is low, such that a long incubation or dwell time is required, measurements will be timed accordingly so that excess data is not taken. If the reaction involves high affinity components, measurement intervals will be minimized, so that more data points are taken. Incubation and dwell time refer to the period of time in which the sample is in contact with the sensing array at nearly full concentration.

If the characteristics of the sample are unknown, an auto-tuning and data culling method is employed, in which binned low-spatial-resolution data is taken at moderate sensitivity settings and minimized intervals, the resultant differential images are analyzed for change, and once signals become evident or fail to become evident in a given time period, kinetic analyses of reactive areas are used to adjust measurement intervals, sensitivity, and spatial resolution to appropriate levels, while the data that displays no differential is discarded except for a few measurements, such as every fifth, tenth. If, for instance, the reaction becomes evident in the first ten seconds of incubation, measurement will proceed at maximal speed and moderate sensitivity for the duration, binning will continue to be employed and all data will be saved.

Figure 2:
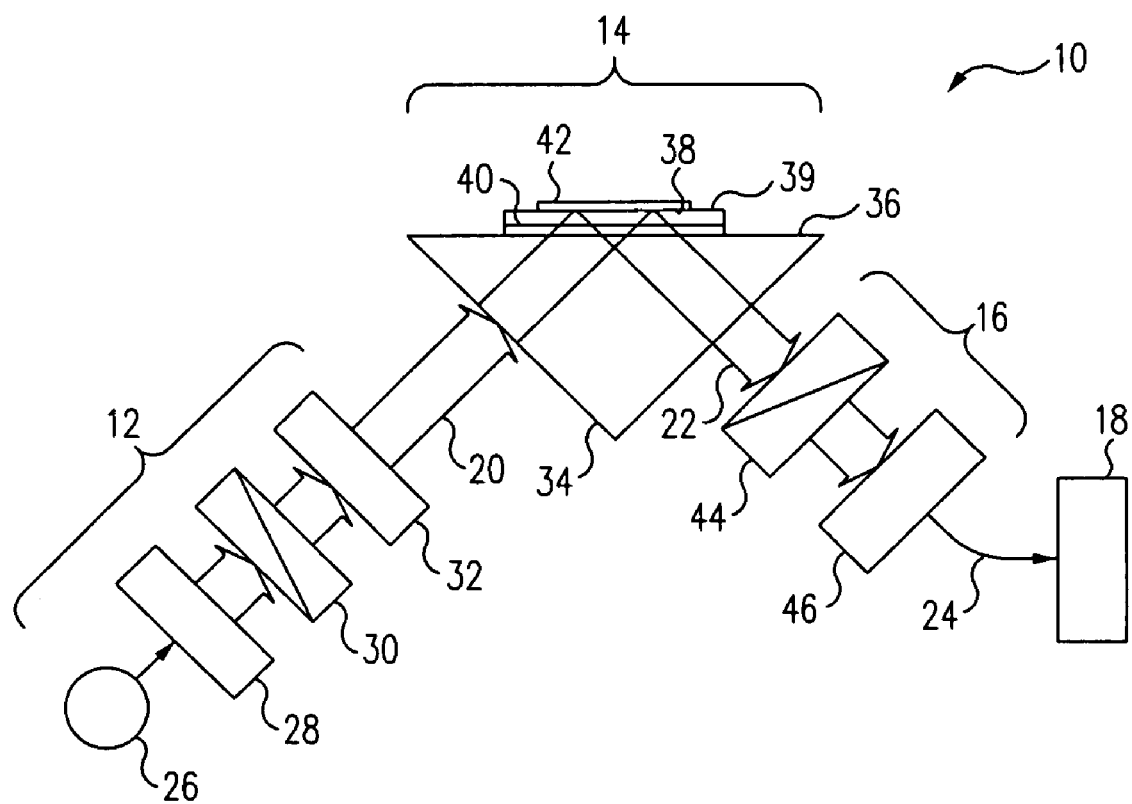
FIG. 2 is a block diagram of an embodiment of the system of FIG. 1.

FIGS. 1 and 2 show an apparatus which implements one embodiment of the invention. As shown in FIG. 1, the apparatus 10 can be described conveniently as comprising three general portions. A first portion includes a polarized light source assembly 12, a second portion includes an optical assembly 14 providing a control layer and/or a light reflection surface, and a third portion includes a polarization-sensitive imaging detector assembly 16 which can employ for example a two-dimensional array detector.

Data from detector assembly 16 is sent by an electrical signal along a connector 24 to processor 18 such as a specially programmed computer and user access system including an image display. Data can be presented as an image, a data table, a graph, or in other forms. The polarized light source assembly 12 passes polarized light of known polarization state 20, which may be varied or varying to optical assembly 14 where a light beam reflection occurs. Reflected light 22, having a changed polarization state, passes to detector assembly 16, where it is recorded spatially over the cross-section of the beam. The recorded data is sent to processor 18 where the change of polarization state is determined to provide a spatially resolved map of changes in polarization state. Where the specimens are presented as an array of discrete spots, each spot will be imaged for its change in polarization state within the spot area.

FIG. 2 shows a more detailed schematic block diagram of one embodiment of apparatus 10. The polarized light source assembly 12 has a light source 26, a beam forming member 28 (if the nature of the light source is such as to make beam forming useful or necessary), a polarizer 30, and an optical retarder 32. In other embodiments, the light source may include a laser and a moving diffuser adapted to produce speckle-offsetting fluctuation of the minima and maxima in the speckle pattern caused by the laser. The moving diffuser may be attached to a mechanical actuator which is preferably a motor and servo-apparatus for providing the speckle offsetting fluctuations. The light beam then proceeds through the beam-forming element 28, the polarizer 30, and the optical retarder 32, exiting light source assembly 12 as light beam 20.

In this embodiment, the optical assembly 14 has an optical element 34 which has an optical surface 36. Also shown is a control layer 38 over optical surface 36, and between them an index matching substance 40. A specimen 42 is positioned on light reflection surface 39 of control layer 38 in one example. In an alternative optical arrangement, a control layer is placed above an index matching substance which in turn is placed above a flat optical member. However constructed, the invention incorporates an optical structure having a light reflection surface and the beam reflects at the reflection surface between entering and leaving the optical structure. In other words, there is a light reflection surface in optical contact with the specimen, such that the evanescent field associated with the total internal reflection interacts with the specimen.

In one embodiment, the post-reflection detector assembly 16 has a polarizer 44 and an imaging detector, for example a two-dimensional array detector 46 and preferably a camera of the CCD or CMOS array type. The post-reflection detector assembly 16 through which the beam 22 passes can alternatively consist of a polarizer member, a beam forming member, and an imaging detector such as a two dimensional array detector or other type of imaging detector.

The processor 18 is a specially programmed computer (or processor) and output means for processing the imagery into a representation of film thickness variations spatially resolved over the cross-section of the area imaged. The imaging is acquired by detecting changes spatially distributed in the local polarization state in the beam's cross-section caused by the total internal reflection. This provides information about the presence and composition in the array of substances on the substrate surface for each resolvable point on the surface. Different polarization state changes are included in the cross-section of the reflected beam indicative of the substances on the specimen in the location in the specimen array corresponding to a position in the detector.

Processor 18 receives the data as an electrical signal (on connector 24) and characterizes the change of polarization state spatially over the two-dimensional array. In processor 18, the analysis and processing is done in one embodiment by comparing the known polarization state of the incoming light from the light source assembly 12 with the changed polarization state of the reflected light 22, spatially resolved two-dimensionally within the beam which provides a map of spatially distributed points or spots in the specimen array. The polarization shift is then analyzed by processor 18 to provide information of the presence and properties of elements in the chemical specimen. Other known techniques, such as null processing can be used to determine the change in polarization state.

The processor can be a general or special purpose processor, preferably with network capabilities. It comprises a central processing unit (CPU), a memory, and a network adapter, which are interconnected by a main bus. Other conventional means, such as a display, a keyboard, a printer, a bulk storage device, and a read-only memory (ROM), may also be connected to the main bus. The memory may store network and telecommunications programs and an operating system (OS).

The invention as described above provides an extremely sensitive optical imaging system for real-time imaging of the binding status of biochip array elements on the surface of an optically transparent material such as a glass or plastic chip. An exemplary monitored array of a 15 mm square inscribed in a 20 mm circular field, with discrete specimen spots of size commensurate with the lateral resolution of the imaging optics, results in fully parallel, continuous real-time readout of up to 5 million sensor fields. Sensor sensitivity to surface attachment is in the femtogram/mm.sup.2 range (e.g., one DNA per square micron).

The apparatus of FIG. 1 operates by imaging the pattern of reactions on the biochip. Those reactions produce changes in the height, surface concentration, and/or refractive index of the material that reacts at each spot. The area imaged could be the entire biochip array or a portion of the entire biochip array. By providing an array of spots of different materials, different constituents in test material flowed over the spots bind in a manner which identifies those constituents. By including in a computer memory the positions of the various materials in the different spots of the array, the image produced by the apparatus of FIG. 1 identifies the constituents in the test material and can also determine the rate at which the reactions occur by imaging successively over time. With the apparatus described, height differences can be imaged dynamically over such short periods of time that intermediate height change readings can be recorded and therefore height change rates can be determined as well as allowing comparison of the rate of height change or intermediate amount of height change among the spots on the biochip array.

The processing and display of the image data by processor 18 will now be discussed in greater detail. Typically, microarray experiments have been analyzed at or near the approximate endpoint of reactions, which is presumed to be equilibrium, and have not provided real-time and/or time-resolved information. Endpoint analysis shows whether the experiment has worked or not but does not provide a way for real-time analysis and time-resolved analysis. Disadvantageously, such endpoint analysis does not allow for monitoring of the process under investigation, thus losing kinetic data, affinity data, and other time-resolved data regarding the process. For example, the present invention allows for the detection of time-related affinity data if certain molecules bind to a part of the array at the beginning of an experiment but the binding does not persist until the end of the experiment. Disadvantageously, endpoint analysis would not capture this type of data.

Such endpoint analysis also does not allow for modification or early termination of the experiment if an error occurs, thus wasting time and resources. For example, the present invention allows a user to change certain parameters to focus on an area of the array after viewing the progress of the experiments if so desired. Positive controls may be observed to verify that the chemistry and detection is working. In another example, if an air bubble or other system failure were to arise in the experiments and cause a significant error in the imaging or if the chemistry itself was to fail, the present invention's real-time and/or time-resolved imaging and display allows the user to stop the process and restart or modify the experiments or to correct the system failure. An endpoint analysis after full preparation and completion of the experimental process would be a waste of the precursor materials, money, time, and other experimental resources.

As noted above, in one embodiment, processor 18 includes a specially programmed computer (or processor) and display means for processing the image data in real-time into a representation of film thickness variations time-resolved and spatially-resolved over the cross-section of the area imaged.

Figure 3:
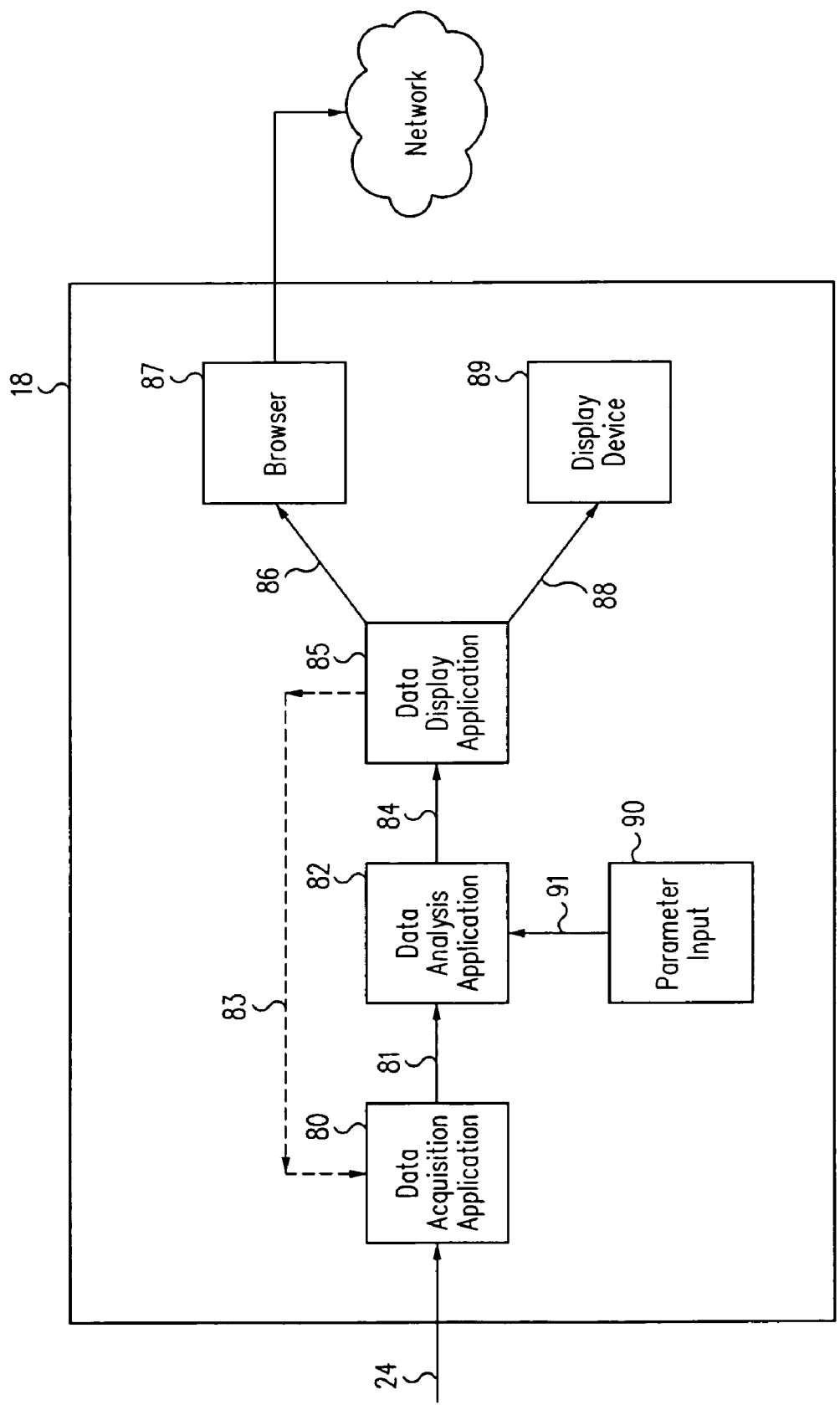
FIG. 3 is a block diagram of a processor in accordance with an embodiment of the present invention.

FIG. 3 illustrates one embodiment of processor 18, which includes a data acquisition application 80 operably coupled to a data analysis application 82 which in turn is operably coupled to a data display application 85. Processor 18 further includes a parameter input interface 90 which is operably coupled to data analysis application 82. A browser 87 operably couples data display application 85 to a communication network, for example the Internet. A display device 89 is operably coupled to data display application 85 for displaying the graphical representations of the image data to a viewer. Both browser 87 and display device 89 are commercially available and known to those of ordinary skill in the art.

The image data may be presented in a hypertext markup language (HTML) format or any similar or succeeding similar language such as PHP: Hypertext Preprocessor (PHP), Active Server Pages, or Perl. This allows for ease of communication and sharing of the image display at remote locations through the Internet or other networking means via various display devices, such as PC display screens, personal digital assistants (PDAs), wireless telephones, and other mobile devices, as well as display near or proximate data acquisition application 80 as shown by dashed line 83.

Data from detector assembly 16 (FIG. 1) is sent along connector 24 in real-time and acquired by data acquisition application 80. The data outputted from data acquisition application 80 is sent along line 81 to data analysis application 82, where the data for multiple microarray spots is analyzed and normalized to quantify an intensity value and corresponding thickness value in real-time and over time (i.e., the data is time-resolved).

Output data from data analysis application 82 is sent along line 84 to data display application 85 which converts the output data into graphical representations for the viewer. In one embodiment, the intensity value is posted in a grid that represents the microarray itself and allows for display of the grid development in real-time and over time as will be explained in greater detail below.

Most microarray experiments include positive controls, negative controls, and/or dilutions over certain areas of the grid. Negative controls should not react during the experiments and are used to determine the background or baseline for the intensity measurements. Theoretically, positive controls and/or dilutions should produce reactions during the experiments and are therefore the brightest (or darkest depending on the display convention) areas of the image. Typically, positive controls on microarrays are set at the margins or other easily located positions, so that they may be used to determine a frame of reference or establish a reference direction, correct image aberration and distortion, or accomplish registration of images to be compared. According to an embodiment of the present invention, many controls are utilized so as to evaluate spot-to-spot variance. Advantageously, the present invention allows for instant feedback on the progress of a large number of experiments, ranging from 1 spot to about 50,000 spots, as real-time and time-resolved information about the microarray can be on display.

Data acquisition application 80 receives the image data from detector assembly 16 (FIG. 1) and can be used to not only receive the image data but to also run the imaging apparatus in one embodiment. In one example, with no intent to limit the invention thereby, data acquisition application 80 can comprise the software package IGOR commercially available from WaveMetrics, Inc. of Lake Oswego, Oreg., appropriately modified to be integrated with at least light source assembly 12 (FIG. 1), optical assembly 14 (FIG. 1), detector assembly 16 (FIG. 1), and data analysis application 82, for automatic data collection and retrieval.

Figure 4:
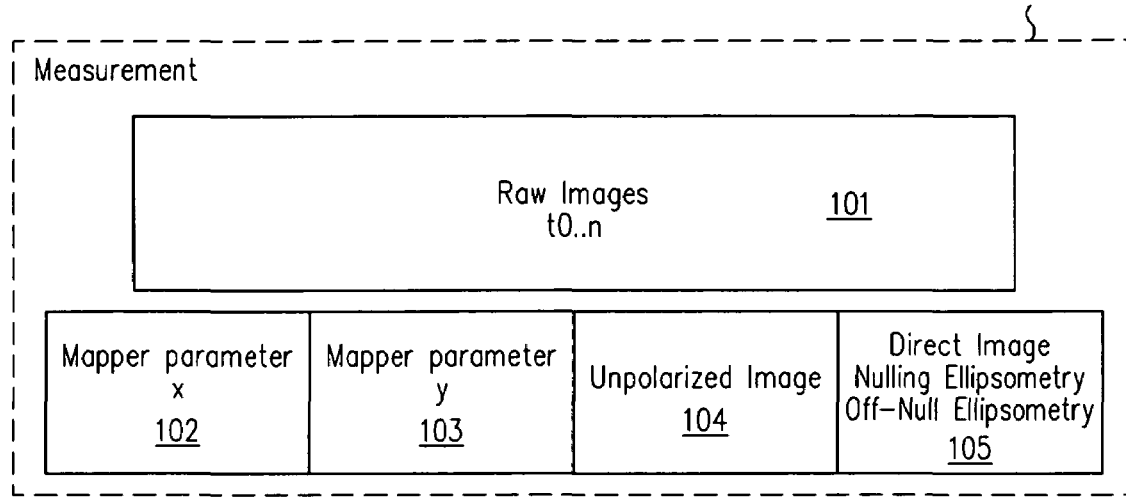
FIG. 4 is a block diagram of image measurements in accordance with an embodiment of the present invention.

FIG. 4 is a block diagram of an example of image measurements that may be collected and processed by data acquisition application 80 (FIG. 3) and sent to data analysis application 82 (FIG. 3) along line 81. Data acquisition application 80 receives raw images 101 taken at predetermined and/or user-selected time intervals "$t_n$" and provides horizontal pixel location/coordinate "x", vertical pixel location/coordinate "y", and an intensity value "z" at the pixel coordinates x and y.

In one embodiment, ellipsometry analysis routines in data acquisition application 80 extract intensity values from the four images 102, 103, 104, and 105 at different polarizer positions (in phase modulation mode) and from these four readings determine the ellipsometric x and y value for each pixel in the image. This data is then fitted to a lookup table based on a selected optical model which results in a thickness map of x,y coordinates and thickness z.

In another embodiment, if nulling or off-null is used, the intensity map of an image at a fixed polarizer position (e.g., "direct" settings are in the IGOR control panel and allow these to be set) is fitted to a Jones or Mueller matrix optical model and a thickness map is generated. The unpolarized image is one of the four images used to generate x,y coordinates and is useful as a demonstration of the imbedded reflectometry measurement capabilities.

Referring back to FIG. 3, data acquisition application 80 outputs image data x, y, and z along line 81 to data analysis application 82 which then analyzes the image data substantially in real-time to produce spatially-resolved images in real-time and over time. Data analysis application 82 is able to evaluate and quantify values inside and outside of each spot in the array. In one example, at predetermined time intervals, the mean value of a spot and a local background value are selected as the parameters used to approximate an intensity value and a corresponding approximation of thickness over a spot normalized against aberrations such as drift and local noise. Thus, data analysis application 82 is able to quantify and qualify the microarray data from data acquisition application 80. In one example, with no intent to limit the invention thereby, data analysis application 82 can be the software package ImaGene commercially available from BioDiscovery, Inc. of El Segundo, Calif., appropriately modified to be integrated at least with data acquisition application 80, parameter input interface 90, and data display application 85 for data retrieval, analysis, and image processing.

Figure 5:
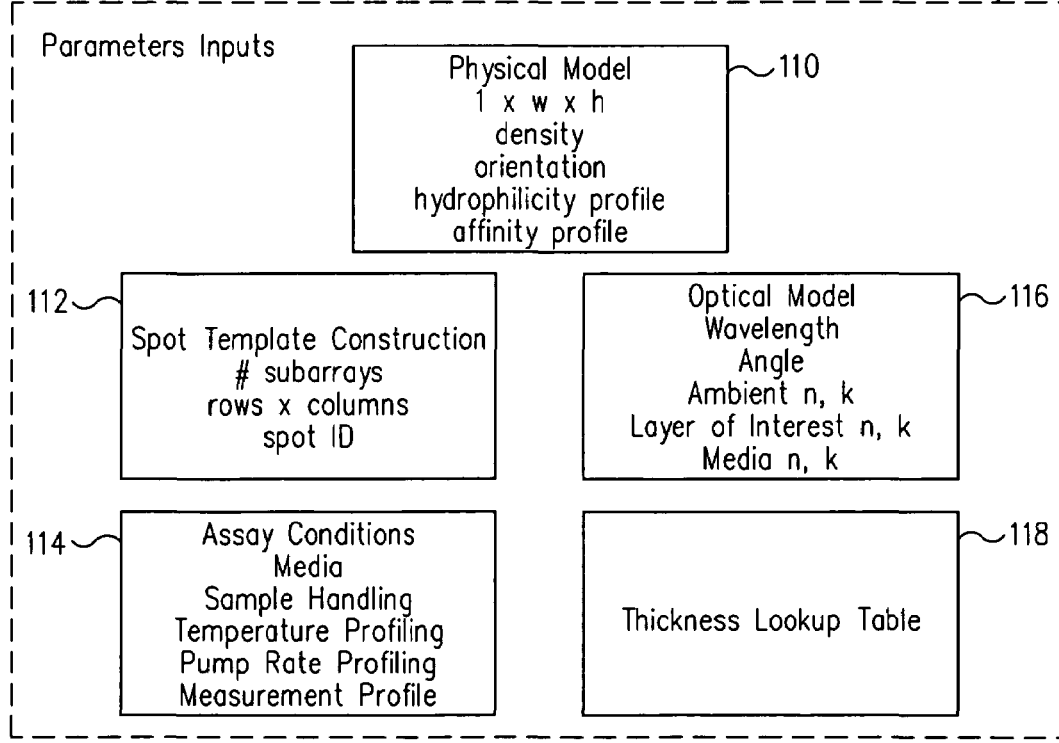
FIG. 5 is a block diagram of parameter inputs in accordance with an embodiment of the present invention.

Parameter input interface 90 is used to input parameters into data analysis application 82 via line 91. FIG. 5 is a block diagram of an example of parameter values that may be inputted into data analysis application 82 from parameter input interface 90 via line 91.

As shown in FIG. 5, parameters may be inputted for the following although not limited thereto: a physical model 110, a spot template construction 112, an optical model 116, assay conditions 114, and a thickness lookup table 118. Parameters for physical model 110 include but are not limited to the length, width, height, density, orientation, hydrophilicity profile, and affinity profile of the array. Parameters for spot template construction 112 include but are not limited to the number of subarrays, rows and columns, and spot identification. Parameters for optical model 116 include but are not limited to wavelength, angle, ambient refractive index (n) and extinction coefficient (k), layer of interest n and k, and media n and k. Parameters for assay conditions 114 include but are not limited to the media type, sample handling, temperature profiling, pump rate profiling, and measurement profile.

Figure 6:
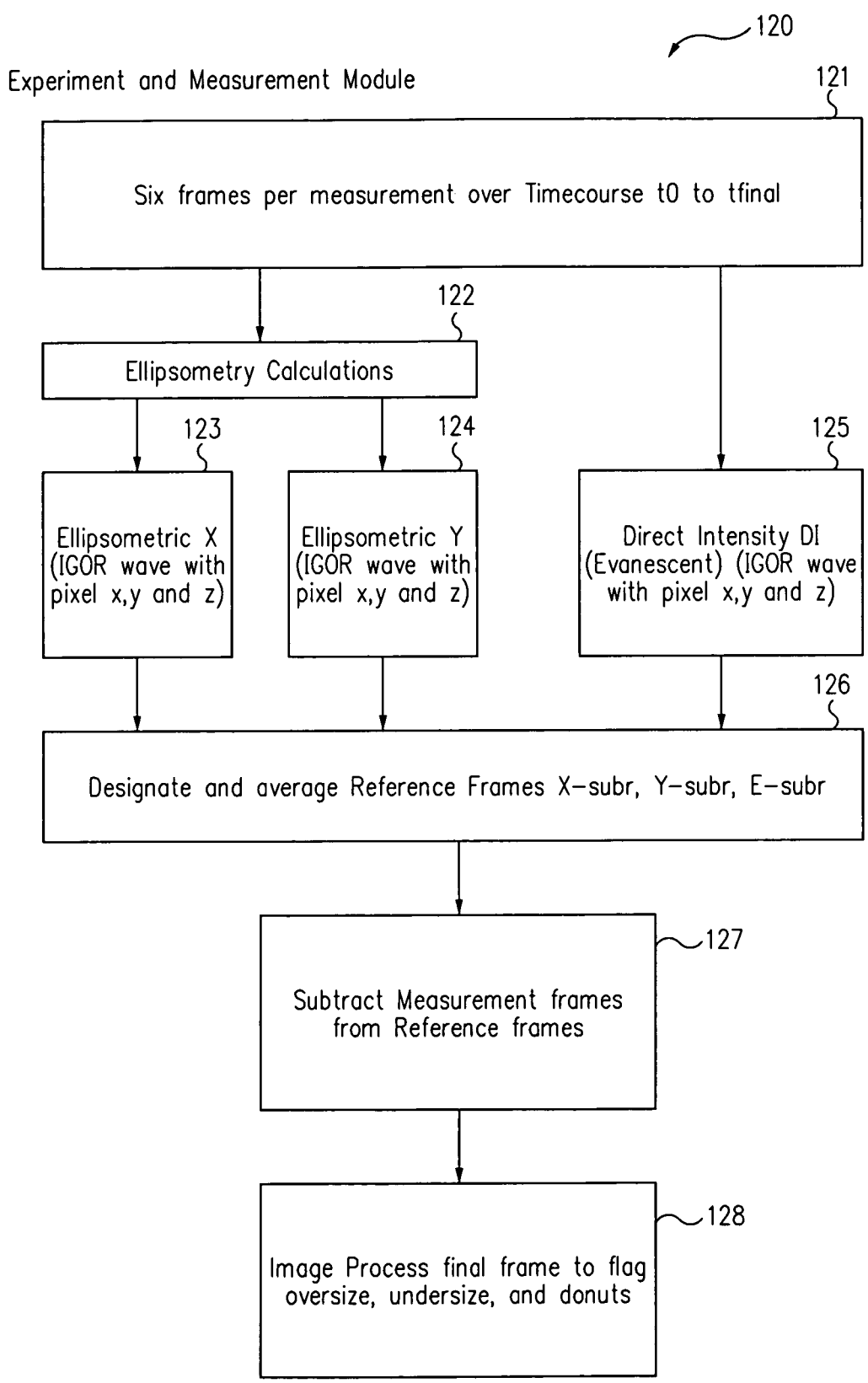
FIG. 6 is a block diagram of a measurement module of an imaging method in accordance with an embodiment of the present invention.

Referring now to FIG. 6, a block diagram is shown illustrating an example of a measurement module 120 of an imaging method that can be utilized by data acquisition application 80 and data analysis application 82. In step 121, six frames (a frame is a single still image from a dynamic series) per measurement are taken over timecourse $t_0$ to $t_{final}$. The raw data is processed in step 122 using ellipsometry calculations to calculate measured ellipsometric X values and measured ellipsometric Y values 123 and 124, respectively. The raw data also includes measured intensity values in step 125. Reference frames are designated and averaged in step 126 and then subtracted from the measurement frames in step 127. The final frame or the frame demonstrating the most change from the initial frame is processed in step 128 to flag spots which are oversized, undersized, and donut-shaped.

Figure 7:
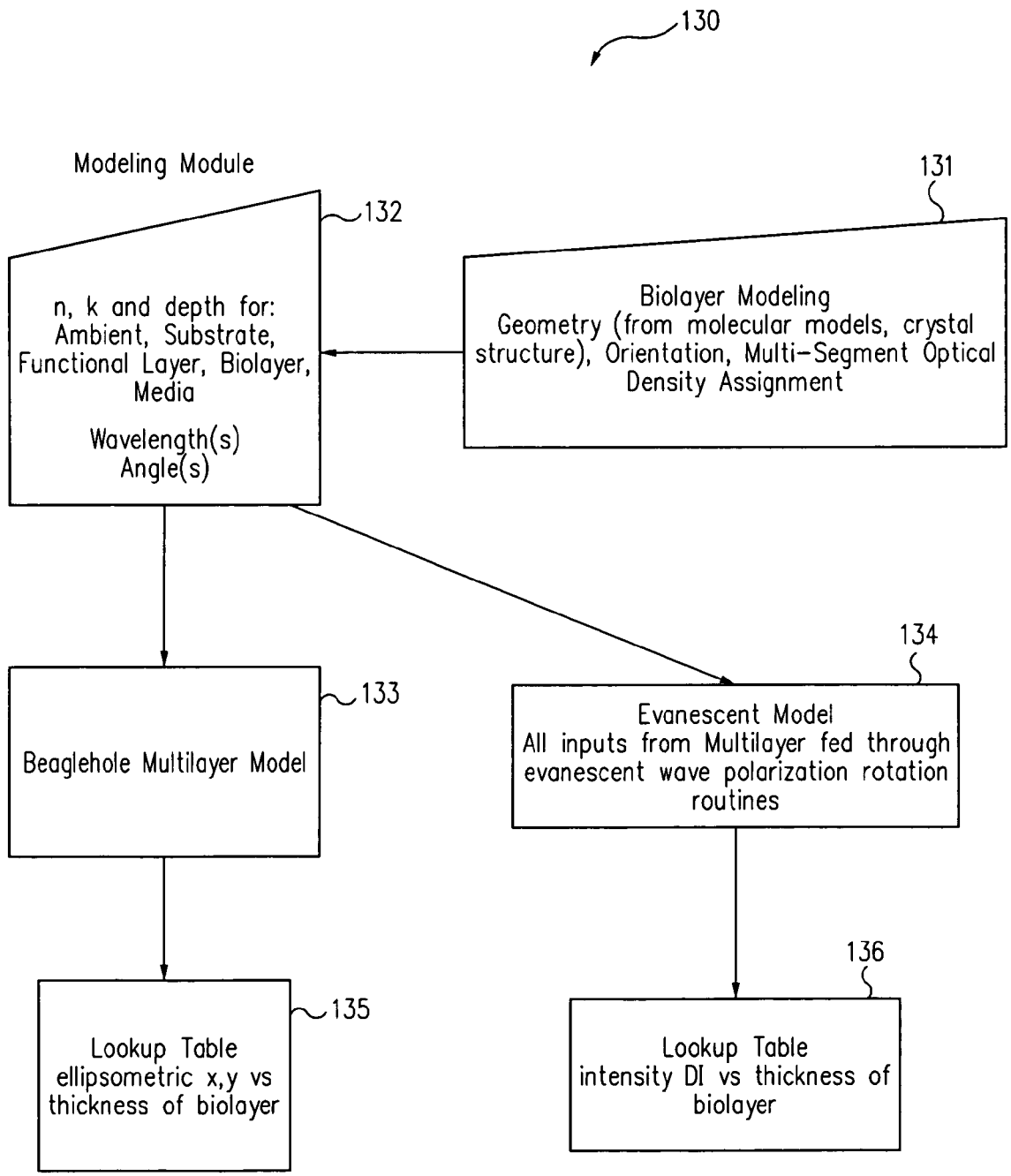
FIG. 7 is a block diagram of a modeling module of an imaging method in accordance with an embodiment of the present invention.

FIG. 7 is a block diagram illustrating an example of a modeling module 130 of an imaging method that can be utilized by data analysis application 82. Parameters to be entered for the physical model 131, for example a biolayer model, include but are not limited to the geometry (from molecular models, crystal structure), orientation, and multi-segment optical density assignment. Parameters for the optical model 132 include the n, k, and depth of ambient, substrate, functional layer, biolayer, and media. Wavelength and angle(s) of the light source is also entered. These modeling parameters are fit into a Beaglehole Multilayer Model 133 and/or an Evanescent Model 134. A lookup table 135 is created including ellipsometric x and y values versus thickness of the biolayer based upon the Beaglehole Multilayer Model. A lookup table 136 is also created including intensity versus thickness of the biolayer based upon the Evanescent Model.

Figure 8:
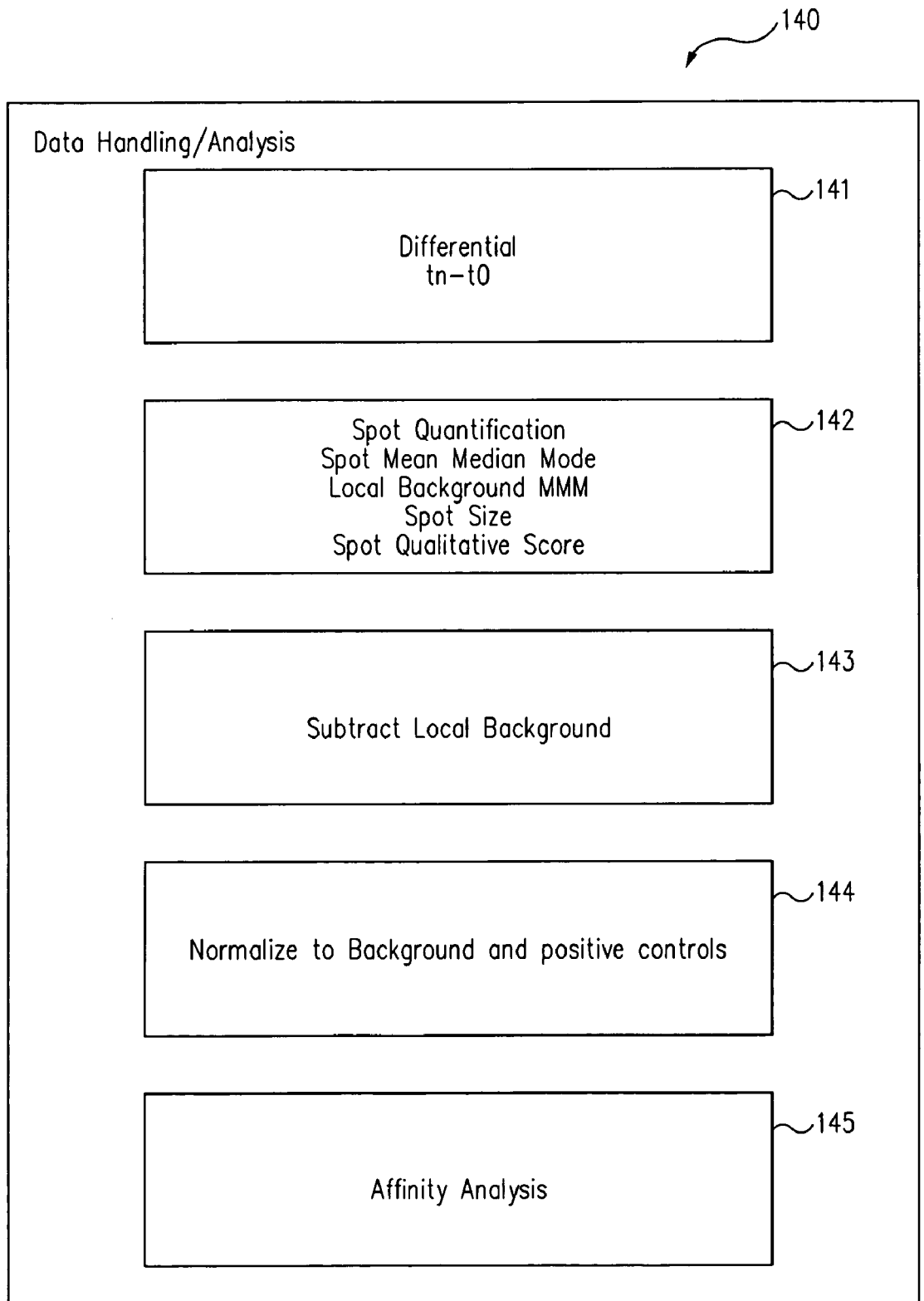
FIG. 8 is a block diagram of a data handling method in accordance with an embodiment of the present invention.

FIG. 8 is a block diagram of an example of a data handling method 140 that can be utilized by data analysis application 82. A differential image is provided by subtracting a reference image ($t_0$) from the latest (current) image ($t_n$) in step 141. Such a differential image can advantageously show change with high resolution in real-time to a viewer when the image is displayed (see, e.g., FIGS. 15-17). A spot is then quantified in step 142 by various parameters including but not limited to a spot mean, median, and mode (MMM), a local background MMM, a spot size, and a spot qualitative score. The local background is then subtracted from the spot value in step 143. The spot value is then normalized to the background and the positive controls in step 144, thus controlling for drift noise or other experimental fluctuations. Finally, an affinity analysis may be conducted based upon the normalized spot value in step 145.

Table 1 below shows a table including possible output from data analysis application 82 but the present invention is not limited to such a list.

TABLE 1

| Output | Definition |
|---|---|
| Field | Name of a field where the spot is located |
| Metarow | Number of metarow in the metagrid where the spot is located |
| Metacolumn | Number of metacolumn in the metagrid where the spot is located |
| Row | Number of row in the subgrid where the spot is located |
| Column | Number of column in the subgrid where the spot is located |
| GeneID | Gene ID information for the spot |
| Flag | Numeric code of the quality flag for the spot (0 - no flag, flag codes 1, . . . , 7) |
| Signal Mean | Pixel intensity averaged over the local signal region |
| Background Mean | Pixel intensity averaged over the local background region |
| Signal Median | Median pixel intensity computed over the local signal region |
| Background Median | Median pixel intensity computed over the local background region |
| Signal Mode | Mode pixel intensity computed over the local signal region (mode corresponds to the pick location in intensity distribution) |
| Background Mode | Mode pixel intensity computed over the local background region |
| Signal Area | Number of pixels in the local signal region |
| Background Area | Number of pixels in the local background region |
| Signal Total | Total pixel intensity summed over the local signal region |
| Background Total | Total pixel intensity summed over the local background region |
| Signal Stdev | Standard deviation of pixel intensities over the local signal region |
| Background Stdev | Standard deviation of pixel intensities over the local background region |
| Shape Regularity | First signal area of a spot is inscribed into a circle. Than number of non-signal pixels that fall within this circle is computed and divided by circle's area. This ratio is subtracted from 1 and is called "shape regularity" |
| Ignored Area | Area of ignored regions directly neighboring ("touching") the signal area is computed |
| Spot Area | Signal Area plus Ignored Area |
| Ignored Median | Median pixel intensity computed over the local ignored region |
| Area To Perimeter | This quality measure defines spot's circularity. Area of a spot is divided by a square of spot perimeter and multiplied by $\pi 4$. As a result, this measure ranges from 0 (highly non-circular shape) to 1 (a perfect circle) |
| Open Perimeter | Computes the proportion of signal perimeter that touches the border of rectangular snip around the spot |
| XCoord | X coordinate (in pixels) of grid circle corresponding to the spot |
| YCoord | Y coordinate (in pixels) of grid circle corresponding to the spot |
| Diameter | Diameter (in pixels) of grid circle corresponding to the spot |
| Position Offset | Offset (in pixels) of the center of the grid circle from the expected position in the grid |
| Offset X | X offset (in pixels) of the center of the grid circle from the expected position in the grid |
| Offset Y | Y offset (in pixels) of the center of the grid circle from the expected position in the grid |
| Expected X | X coordinate of expected position of the circle in the grid. Expected position in the grid is computed fitting least square lines to circle centers in every row and column |
| Expected Y | Y coordinate of expected position of the circle in the grid. Expected position in the grid is computed fitting least square lines to circle centers in every row and column |
| CM-X | X coordinate of the center of the mass of spot's signal region |
| CM-Y | Y coordinate of the center of the mass of spot's signal region |

TABLE 1-continued

| Output | Definition |
| --- | --- |
| CM Offset | Offset (in pixels) of the spot's center of the mass from the expected position in the grid |
| CM Offset-X | X offset (in pixels) of the spot's center of the mass from the expected position in the grid |
| CM Offset-Y | Y offset (in pixels) of the spot's center of the mass from the expected position in the grid |
| Min Diam | Diameter of the circle inscribed into the spot's signal region |
| Max Diam | Diameter of the circle, the spot's signal region can be inscribed in |
| Control | Name of a control type for current spot (no name means the spot is not a control spot) |
| Failed Control | 0 if the control passed all tests, 1 if at least one of the tests failed |
| Background Contamination Present | 0 if the spot passed background contamination test, 1 if it did not |
| Signal Contamination Present | 0 if the spot passed signal contamination test, 1 if it did not |
| Ignored % failed | 0 if the spot passed ignored percentage test, 1 if it did not |
| Open Perimeter Failed | 0 if the spot open perimeter test, 1 if it did not |
| Shape Regularity Failed | 0 if the spot passed shape regularity test, 1 if it did not |
| Perim-To-Area | 0 if the spot passed perimeter-to-area test, 1 if it did not (see section 1.4) |
| Offset failed | 0 if the spot passed offset test, 1 if it did not |
| Empty spot | 1 if the spot was qualified as empty, 0 if it was not |
| Negative spot | 1 if the spot was qualified as negative, 0 if it was not |

Figure 9:
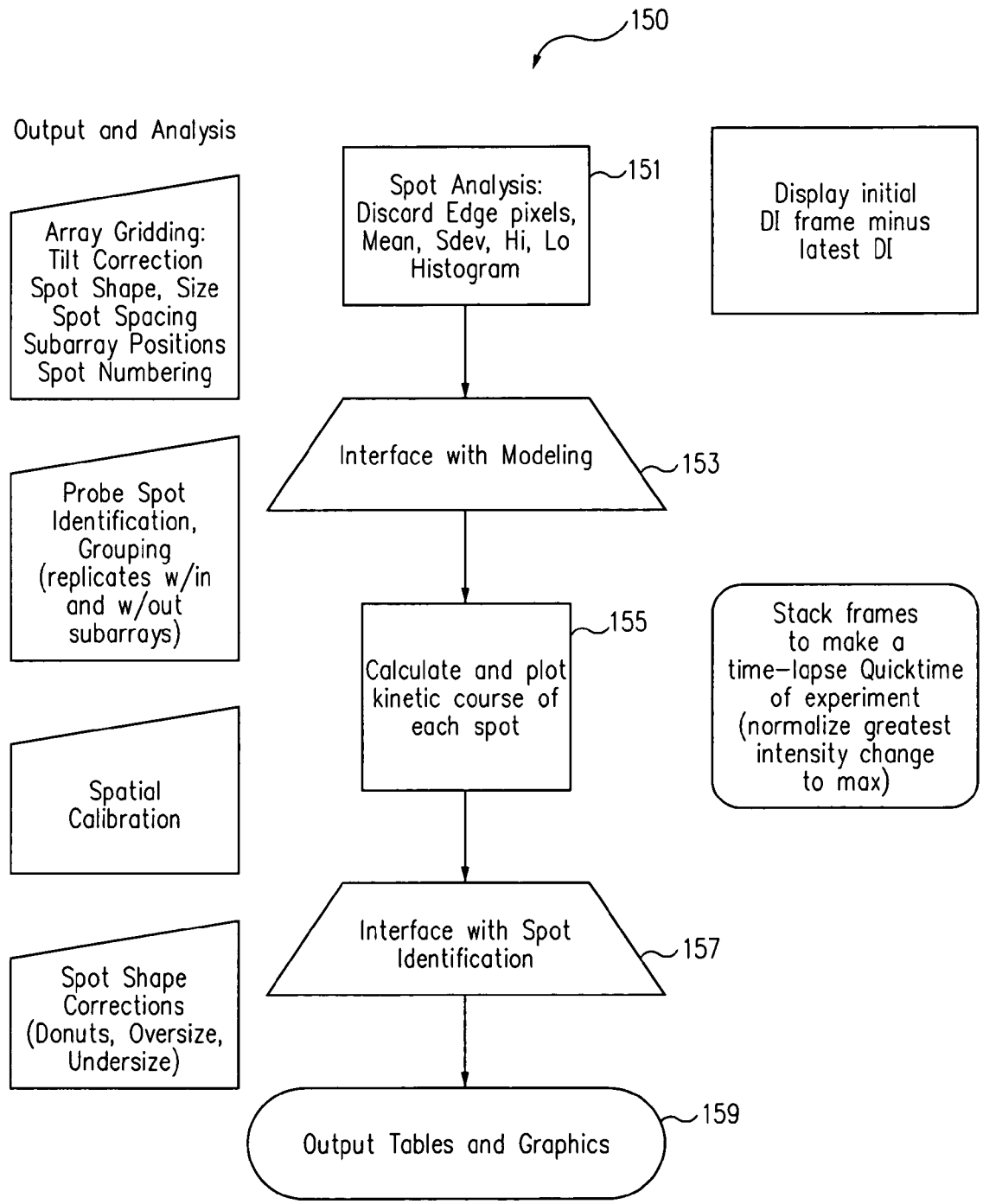
FIG. 9 is a block diagram of an image data analysis method in accordance with an embodiment of the present invention.

Referring now to FIG. 9, a block diagram is shown illustrating an example of an image data analysis method 150 of the present invention. At step 151, each of the spots in the microarray are measured and the mean value of each spot is calculated using the measurement module. The modeling module is then called at step 153 to calculate thickness of the biolayer. The kinetic course of each spot is then calculated and plotted at step 155. Spot identification information is called at step 157 and image output tables and graphics are displayed in real-time and over time at step 159.

Referring back to FIG. 3, output from data analysis application 82, such as text files, XML files, or other appropriately formatted data, is sent via line 84 to data display application 85 which further processes the data for display. Data display application 85 includes commercially available database and spreadsheet programs such as Microsoft Access and Microsoft Excel which can receive data from data analysis application 82 and can then be manipulated by an algorithm for graphical representation of the data.

Figure 10:
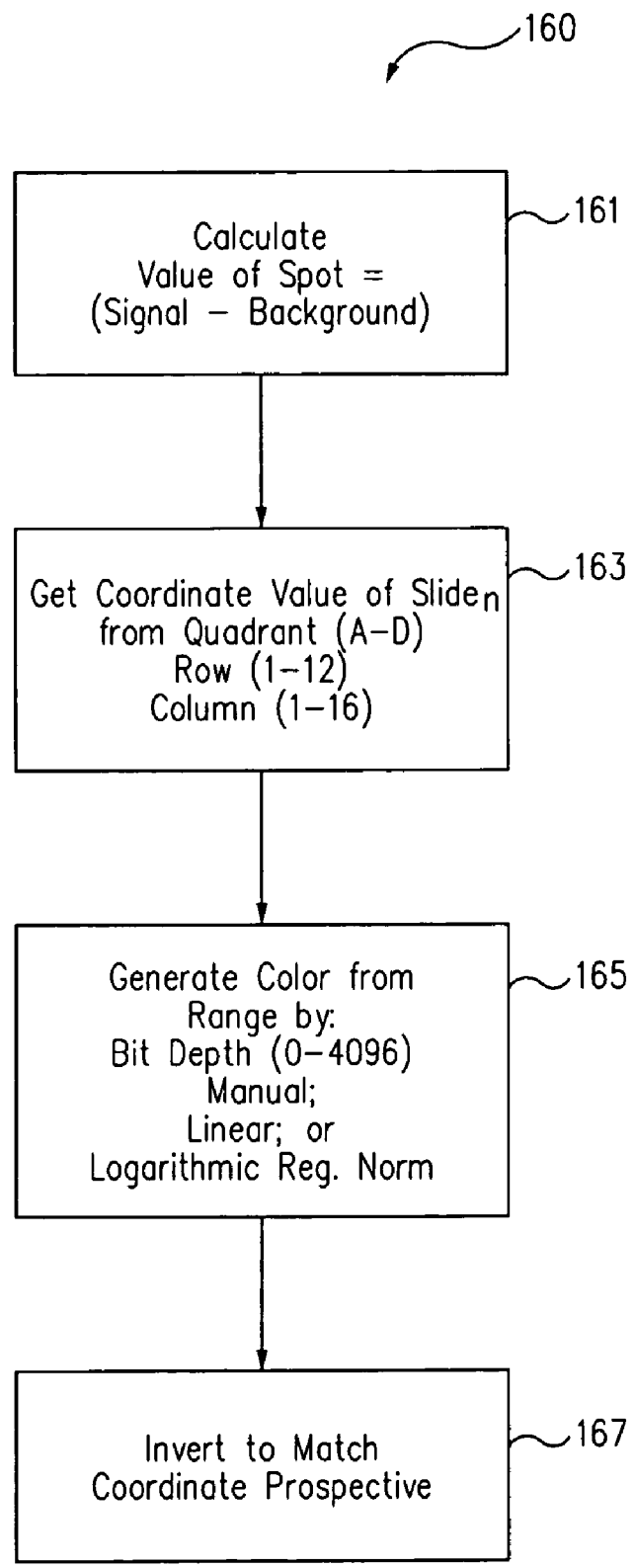
FIG. 10 is a block diagram of an image data display method in accordance with an embodiment of the present invention.

FIG. 10 is a flowchart of an example of an image data display method 160. The value of a spot is first calculated by subtracting a background value from the signal (step 161). The coordinates of the spot are retrieved, based upon quadrant A-D, row 1-12, and column 1-16 (step 163). Next, a color is generated according to a range such that change of thickness (shown through a change in color/contrast of the spot) is easily visible to the user (step 165). In one example, if the spot value is 8-bits, the image data display method of FIG. 10 assigns a gray scale value to every number between 0 and 4,096. If the spot value is 16-bits, a gray scale value is assigned to every number between 0 and 65,000. At the final step 167, the method inverts the y coordinate values for redisplay based on the viewer's perspective since the image view is from below the microarray in this example.

Table 2 below shows an example of software code for displaying time-resolved values of the ellipsometric z shift data, which is proportional to film thickness change, according to the method illustrated by the flowchart in FIG. 10.

TABLE 2

```
 1: <%
 2: Set Conn1 = Server.CreateObject("ADODB.Connection")
 3: MdbFilePath = Server.MapPath("../private/maven.mdb")
 4: Conn1.Open "Driver={Microsoft Access Driver (*.mdb)};
    DBQ=" &MdbFilePath &";"
 5:
 6: Set diff = Conn1.Execute("SELECT value FROM diff"&
    Request("n") &" ORDER BY field,row,column")
 7: %>
 8:
 9: <%
10:
11: Function GenerateColor(NumberToConvert, MinValue, MaxValue)
12:
13:     If NumberToConvert <= MinValue Then
14:         GenerateColor = "#000000"
15:         Exit Function
16:     End If
17:
18:     If NumberToConvert >= MaxValue Then
19:         GenerateColor = "ftffffff"
20:         Exit Function
21:     End If
22:
23:     Numerator = NumberToConvert – MinValue
24:     Denominator = MaxValue – MinValue
25:
26:     ScaledValue = Round(((Numerator * 255) / Denominator), 0)
27:     GenerateColor = lCase("#" &Right("0" &
    Hex(ScaledValue), 2) &Right("0" &
    Hex(ScaledValue), 2) &Right"0" &Hex(ScaledValue), 2))
28:
29: End Function
30:
31: %>
32: <html>
33: <head>
34: <title>Maven</title>
35: </head>
36: <body bgcolor="#000000">
37:
38: <table cellspacing="0" cellpadding="0" border="0"
    width="100%" height="100%">
39: <tr><td align="center">
40:
41: <!-- main start -->
42: <table cellspacing="0" cellpadding="10" border="0">
43: <tr><td>
44:
45: <!-- 1 start -->
46:
47:
48: <table cellspacing="20">
49: <%
50: For Quadrant = 1 to 4
51:     Select Case Quadrant
52:         Case 1: QuadrantLetter = "C"
53:         Case 2: QuadrantLetter = "D"
54:         Case 3: QuadrantLetter = "A"
55:         Case 4: QuadrantLetter = "B"
56:     End Select
57: %>
58:     <%If Quadrant Mod 2=1 Then%><tr><%End If%>
59:     <td>
60:
61:     <table cellspacing="4" cellpadding="0" border="0">
62:
63: <%
64:     Set diff = Conn1.Execute("SELECT value FROM diff"&
    Request("n") &" WHERE Field = '" &
    QuadrantLetter &"' ORDER BY row,column")
65:     For Row = 1 To 12
66: %>
67:         <tr>
68: <%
69:         For Column = 1 To 16
```

TABLE 2-continued

```
 70: %>
 71:
 72: <%
 73: ' ranges for different slides
 74: ' slide # = min,max
 75: '00 = 0,0
 76: '01 = 4320,4900
 77: '02 = 2660,3060
 78: '03 = 10550,11000
 79: '04 = 6220,6700
 80: '05 = 1520,2200
 81: '06 = 1240,1900
 82: '07 = 60,500
 83: '08 = 1630,2200
 84: '09 = 90,700
 85: '10 = 70,650
 86: '11 = 90,650
 87: '12 = 100,800
 88: '13 = 3260,3900
 89: '14 = 10890,11700
 90: '15 = 7620,8500
 91: '16 = 9630,10500
 92: '17 = 12450,13500
 93: '18 = 5970,6950
 94: '19 = 7730,8920
 95: '20 = 8490,9500
 96: '21 = 8500,9500
 97: '22 = 2580,3550
 98: '23 = 10050,11000
 99: '24 = 8000,8700
100: '25 = 6120,6720
101: '26 = 6360,7100
102: '27 = 6050,6800
103: '28 = 2600,3200
104: '29 = 6920,7500
105: %>
106:       <td
      bgcolor="<%=GenerateColor(diff("value"),2600,3200)%>"><img
      src="cover.gif" width="15" height="15" alt=""></td>
107: <%
108:         diff.MoveNext
109:       Next
110: %>
111: <%
112:       Next
113: %>
114:       </tr>
115:
116:
117:     </table>
118:
119:     </td>
120:     <%If Quadrant Mod 2=0 Then%></tr><%End If%>
121: <%
122: Next
123: Set diff = Nothing
124: %>
125: </table>
126:
127:
128: </td></tr>
129: </table>
130: <!-- main end -->
131:
132: </td></tr>
133: </table>
134:
135: </body>
136: </html>
137:
138: <%
139: Set diff = Nothing
140: Conn1.Close
141: Set Conn1 = Nothing
142: %>
```

Figure 11:
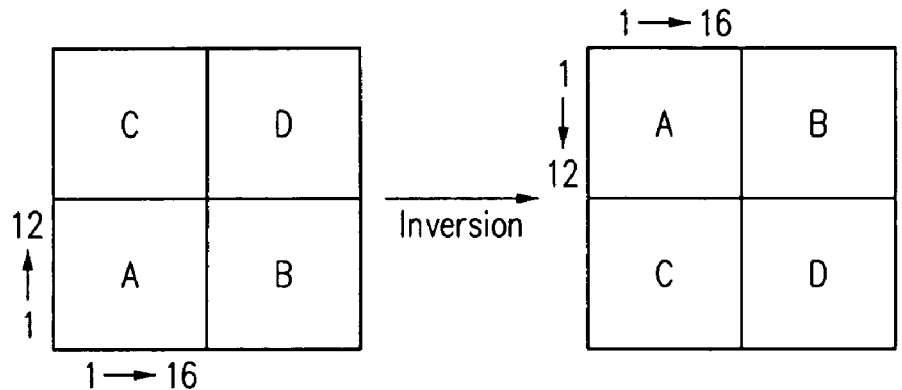
FIG. 11 is a block diagram of coordinate inversion of an image slide in accordance with an embodiment of the present invention.

FIG. 11 is a block diagram of the coordinate inversion of an image slide noted above with respect to FIG. 10.

Figure 12:
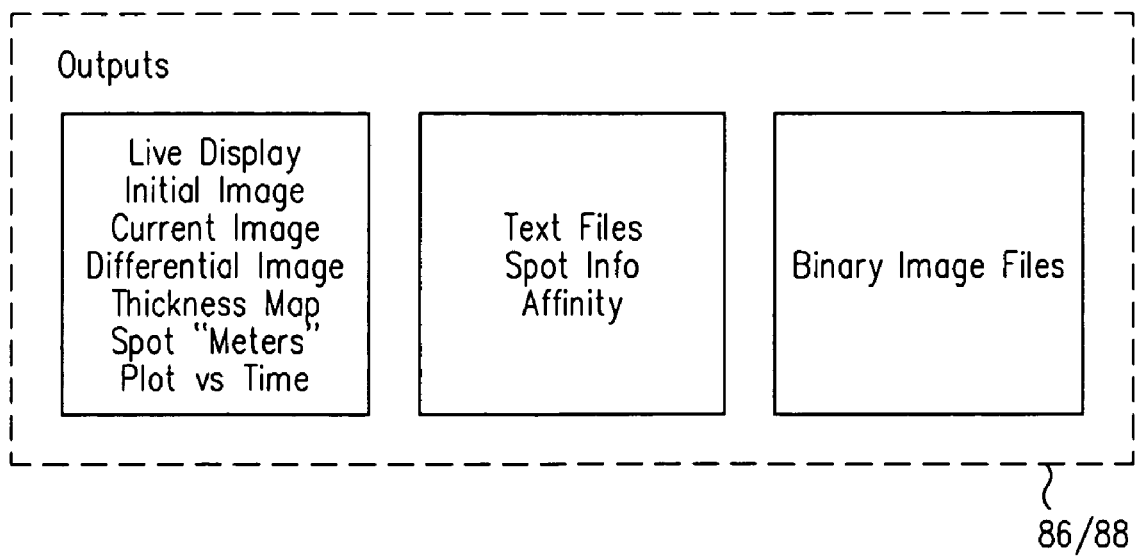
FIG. 12 is a block diagram of outputs in accordance with an embodiment of the present invention.

FIG. 12 is a block diagram of an example of outputs from data display application 85 which can be sent via lines 86 and/or 88 to browser 87 and display device 89, respectively. Outputs include but are not limited to real-time (live) displays, text files, and binary image files (x, y, and z values from IGOR). Real-time displays can include but are not limited to an initial image, a current image, a differential image, a thickness "map" which shows thickness over the microarray, spot "meters", and a plot of thickness versus time. Text files can include but are not limited to spot information and related affinity information.

Figure 13:
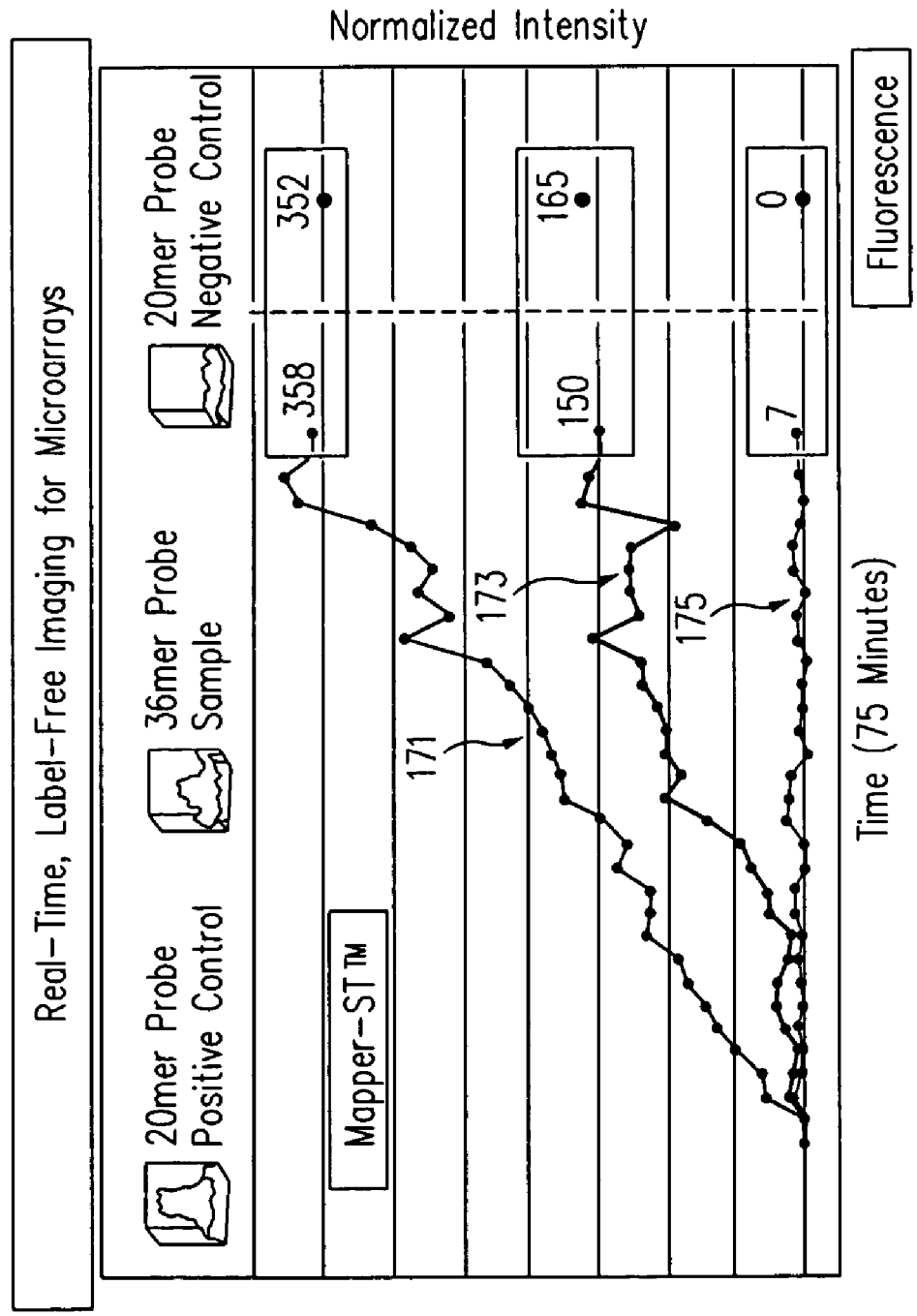
FIG. 13 is a graph of specimen spot intensity over time.

FIG. 13 is a graph of specimen spot intensity over time in seconds. Positive and negative controls are utilized to normalize the measured data as mentioned above. The graph demonstrates a steeper affinity slope, indicating fast interaction and more change, at the end of 75 minutes in the positive control 171 than in the other specimen spots, sample 173, and negative control 175. Correlation with labelled and conventionally scanned data is also demonstrated.

Figure 14:
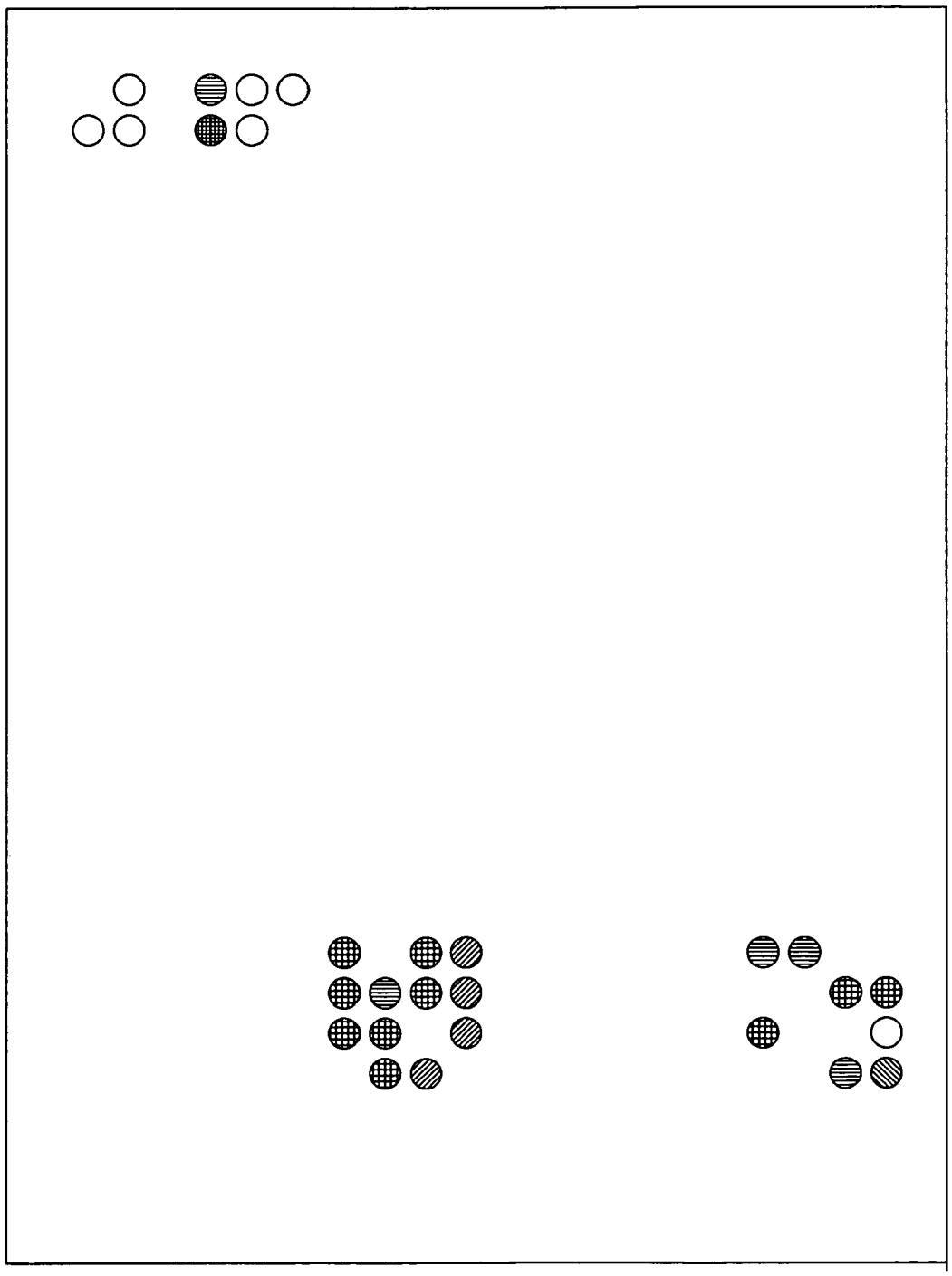
FIG. 14 is a display of a frame of time-resolved specimen spot intensity.

FIG. 14 is an example of an html display of a frame of time-resolved specimen spot intensity. In one example, each frame constitutes 78 kilobytes rather than the typical 600 kilobytes to 30 megabytes of the differential image. The data economy is thus demonstrated.

It will be apparent that FIGS. 13 and 14 are just two of a variety of graphical representations of the time-resolved image data which can be provided. In one example, time-resolved image data could be displayed in various tables, graphs, and charts.

Figure 15:
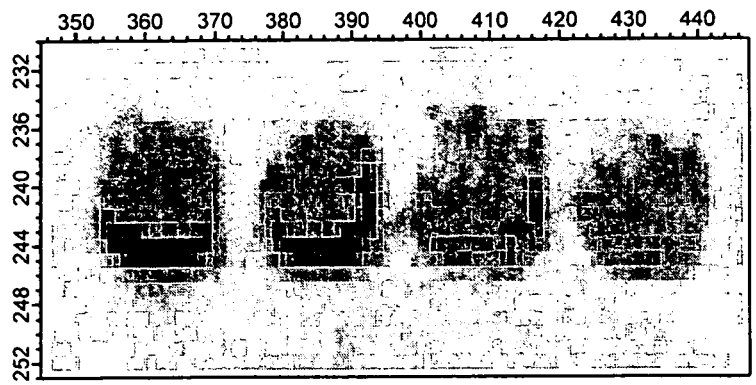
FIG. 15 illustrates a TIFF image of time-resolved specimen spot intensity at a first time.
Figure 16:
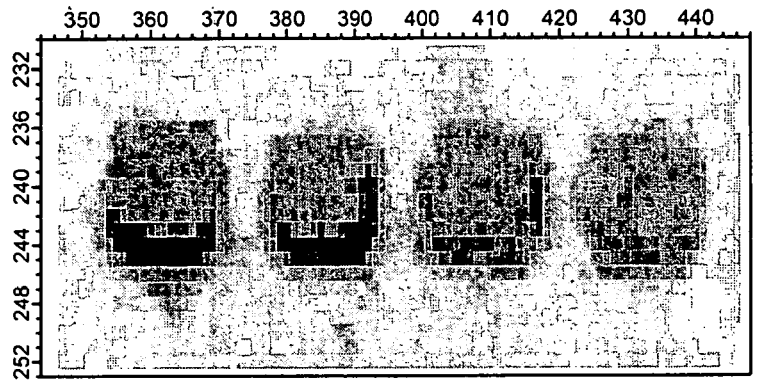
FIG. 16 illustrates a TIFF image of time-resolved specimen spot intensity at a second time.
Figure 17:
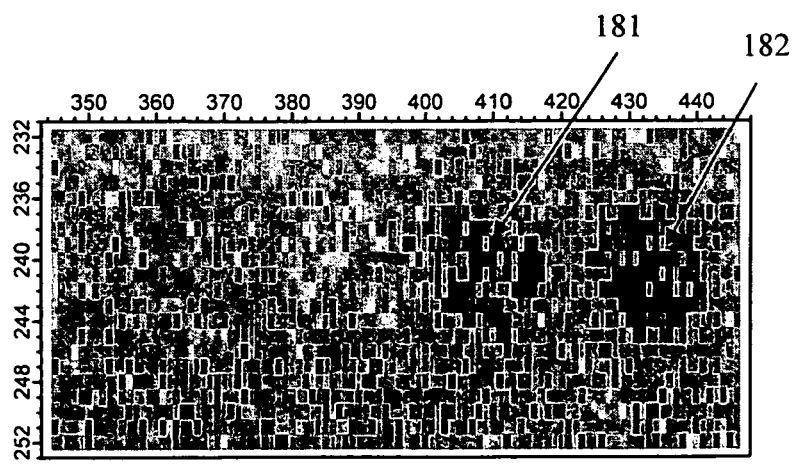
FIG. 17 illustrates a differential TIFF image between the images shown in FIGS. 15 and 16.

For example, FIGS. 15-17 illustrate graphical representations of image subtraction, specifically subtraction of a reference image (FIG. 15) from each subsequent image (FIG. 16) in a time-resolved sequence of images, resulting in a "differential image" (FIG. 17) that may increase the practical sensitivity and dynamic range of the resultant image upon digitization. For example, if measurements can be made to seven significant digits, and a surface is monitored over time for small changes, but the surface already has irregularities such as gross features, roughness, or a tilt, much of the range of the resultant digitized image will be occupied by the "background" and not the data. 16-bit TIFF images are currently the most common and practical format for scientific imaging and analysis, due to dynamic range of the detection methods used to create them and the data storage considerations of larger bit-depth images. With 65,500 levels per pixel, if the roughness and tilt remain in the image, the small surface changes of interest will comprise only a tiny range within the image, and comparison to the reference image will reveal no discernable changes. However, if the differential image is generated before conversion to an image format such as a 16-bit TIFF, the full bit-depth of the image format is utilized for just the data of interest, rather than the background.

In FIGS. 15 and 16, a surface is measured at two different times, producing an initial and subsequent binary image. The initial image is subtracted from the subsequent image, producing the differential image in FIG. 17. All three images are then digitized into 16-bit TIFFs by identical means. A region of interest of the initial, subsequent, and differential TIFF images is displayed and analyzed. As can be easily seen in FIG. 17, a differential image of areas 181 and 182 show a change in the areas whereas a change is difficult to notice when visually comparing the individual binary images of FIGS. 15 and 16.

Figure 18:
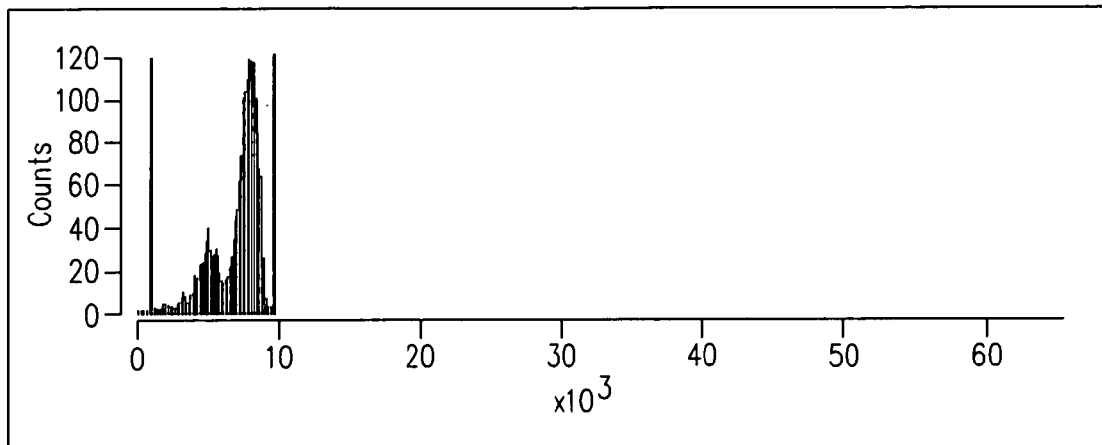
FIGS. 18 and 19 are histograms of the TIFF images shown in FIGS. 16 and 17.
Figure 19:
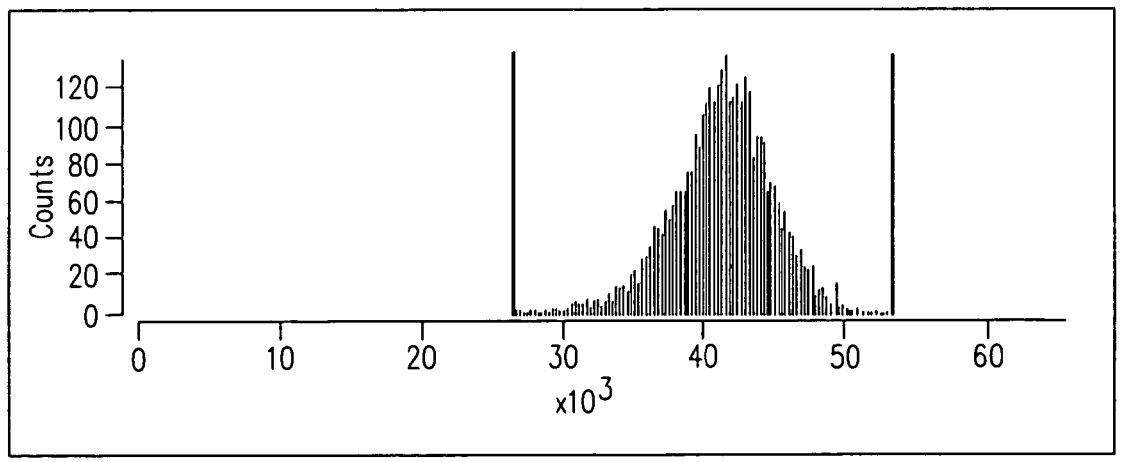

Referring now to FIGS. 18 and 19, the initial and subsequent images have a 10,000 count range, containing 40 distinct levels, while the differential image covers a 25,000 count range with 112 levels. The changes would be undetectable if comparing the post-digitization TIFF images.

Advantageously, the present invention allows for clear visualization of experimental progress in a microarray containing a plurality of specimen spots. A user interface with display device 89 is also within the scope of the present invention such that information regarding the graphical representations may be provided to the user at his request. For example, if the user were to position a pointer at a certain area of the graphical representation, actual data regarding the microarray, such as X and Y coordinates, thickness value, and gene ID of that sensing spot, could be displayed for the user.

The present invention also allows for ease of communication of a microarray's experimental progress outside of the laboratory to a plurality of parties. It is apparent that the present invention is not limited to displaying data on a single display device 89 (FIG. 3) but may be used to display data on a plurality of display devices using browser 87. Advantageously, such communication of the real-time and time-resolved image data allows for enhanced collaboration between researchers on experiments in a real-time setting. The data stream is smaller than would be required to transmit the images, which are at least 600 kilobytes.

The above-described embodiments of the present invention are merely meant to be illustrative and not limiting. It will thus be obvious to those skilled in the art that various changes and modifications may be made without departing from this invention in its broader aspects. For example, while communication channels within the figures, for example FIG. 3, have been referred to as lines, it should be understood that what are called lines can be buses capable of carrying a plurality of signals (either digital or analog as appropriate) in parallel or can even be wireless communication channels. Furthermore, although reference is made to biochips in the examples above, the procedure and the results apply generally to chemically sensitive materials on a light reflection surface. Therefore, the appended claims encompass all such changes and modifications as falling within the true spirit and scope of this invention.

We claim:

1. An apparatus for imaging, comprising:
   a light source emitting a polarized light beam;
   an optical assembly including a light reflection surface, wherein the light beam from the light source is reflected by the light reflection surface to provide an evanescent field adjacent the light reflection surface, the light reflection surface being adapted to allow placing thereon a specimen array such that the specimen array in the evanescent field causes spatially distributed polarization changes in the cross-section of the light beam;
   a two-dimensional array detector positioned to detect the spatially distributed polarization changes caused by the specimen array; and
   a processor operably coupled to the two-dimensional array detector, the processor processing data from the two-dimensional array detector to provide a two-dimensional representation of the spatially distributed polarization changes occurring in the specimen array in real-time.

2. The apparatus as in claim 1, wherein the specimen array comprises a two-dimensional array formed of multiple fields comprising biomolecular substances.

3. The apparatus as in claim 2, wherein the biomolecular substances are proteins, peptides, and/or polynucleotide sequences.

4. The apparatus as in claim 1, wherein the processor calculates an intensity value of a specimen array spot over time.

5. The apparatus as in claim 4, wherein the processor associates a color value to the calculated intensity value.

6. The apparatus as in claim 1, wherein the processor includes a display device for displaying the two-dimensional representation of the spatially distributed polarization changes occurring in the specimen array.

7. The apparatus as in claim 1, wherein the processor includes a browser application for uploading the two-dimensional representation of the spatially distributed polarization changes occurring in the specimen array to a network.

8. The apparatus as in claim 1, wherein the processor calculates an intensity value differential of a specimen spot in the specimen array.

9. A method of imaging, comprising:
   passing a polarized light beam into an optical assembly including a control layer and a light reflection surface to provide an evanescent field with controlled height and intensity adjacent the light reflection surface, a specimen array in the evanescent field causing spatially distributed polarization changes in the cross-section of the light beam;
   passing the reflected light beam out of the optical structure;
   detecting the spatially distributed polarization changes caused by the specimen array; and
   processing the detected spatially distributed polarization changes to provide a two-dimensional representation of the spatially distributed polarization changes occurring in the specimen array in real-time.

10. The method of claim 9, wherein the specimen array comprises a plurality of discrete specimen spots and the image is provided for each of the discrete specimen spots.

11. The method of claim 9, further comprising using the spatially distributed polarization changes to determine two-dimensionally distributed presence and/or properties of the specimen array constituents.

12. The method of claim 9, wherein the specimen array is in a micro-titer plate.

13. The method of claim 12, further comprising:
    resolving the spatially distributed polarization changes for matching positions in the micro-titer plate; and
    analyzing the polarization changes to determine desired characteristics in each position.

14. The method of claim 9, further comprising analyzing the polarization changes to determine the binding characteristics of each discrete specimen spot.

15. The apparatus of claim 1, wherein the processor is adapted to calculate at least one time-resolved value of the data from the detector including a thickness value of a specimen spot in the specimen array.

* * * * *